United States Patent [19]

Kreighbaum et al.

[11] 4,186,131

[45] Jan. 29, 1980

[54] PHENYLTETRAZOLYLOXY PROPANOLAMINES

[75] Inventors: William E. Kreighbaum; William T. Comer, both of Evansville, Ind.

[73] Assignee: Mead Johnson & Company, Evansville, Ind.

[21] Appl. No.: 889,780

[22] Filed: Mar. 24, 1978

Related U.S. Application Data

[63] Continuation-in-part of Ser. No. 789,481, Apr. 21, 1977, abandoned.

[51] Int. Cl.$^2$ .................... C07D 257/04; A61K 31/41
[52] U.S. Cl. .................... 548/251; 424/269; 548/215

[58] Field of Search .................... 260/308 D

[56] References Cited

PUBLICATIONS

Fuson, "Adv. Org. Chem.", pp. 589–599, Wiley (1950).

*Primary Examiner*—Glennon H. Hollrah
*Assistant Examiner*—D. B. Springer
*Attorney, Agent, or Firm*—R. E. Carnahan; R. H. Uloth

[57] ABSTRACT

1-Secondary-amino-3-(1-phenyl and substituted phenyl-5-tetrazolyloxy)-2-propanols are new compounds which are useful as cardiovascular agents having antiarrhythmic and β-adrenergic blocking actions.

32 Claims, No Drawings

PHENYLTETRAZOLYLOXY PROPANOLAMINES

REFERENCE TO RELATED APPLICATION

This application is a continuation-in-part of our prior copending application Ser. No. 789,481 filed Apr. 21, 1977, now abandoned.

FIELD OF THE INVENTION

This invention is concerned with heterocyclic carbon compounds of the tetrazole series and with drug bio-affecting and body-treating processes employing these substances as active ingredients.

DESCRIPTION OF THE PRIOR ART

A substantial body of prior art has developed during the last ten years involving compounds of the 3-aryloxy-2-hydroxypropylamine series which have β-adrenergic receptor blocking activity and are useful in the treatment of cardiovascular diseases including hypertension, angina pectoris, and cardiac arrhythmias. These structures are typified by the substance 1-isopropylamino-3-(1-naphthoxy)-2-propanol which is currently in medical use under the non-proprietary name propranolol. Propranolol and a related group of naphthoxypropanolamines are the subject of U.S. Pat. No. 3,337,628 patented Aug. 22, 1967. A large number of patents have been granted since that time on carbocyclic ethers in which other aromatic rings replace the naphthoxy group of propranolol. Many of these compounds are in the phenoxy series and others are phenoxy compounds with fused heterocyclic rings. More recently, (heterocyclo)oxypropanolamine ethers have been described in which the carbocyclic ring of the foregoing compounds is replaced with a heterocyclic ring. Representative compounds of this type are found in the following patents and publications.

3-(3-tert.-Butylamino-2-hydroxypropoxy)-2-methyl-4-pyranone, U.S. Pat. No. 3,828,076, patented Aug. 6, 1974.

3-Morpholino-4-(3-tert.-butylamino-2-hydroxypropoxy)-1,2,5-thiadiazole, U.S. Pat. No. 3,891,639, patented June 24, 1975.

2-(3-tert.-Butylamino-2-hydroxypropoxy)-3-phenylpyrazine, U.S. Pat. No. 3,946,009, patented Mar. 23, 1976.

2-(3-tert.-Butylamino-2-hydroxypropoxy)thiazole, U.S. Pat. No. 3,982,010, patented Sept. 21, 1976.

5-(3-tert.-Butylamino-2-hydroxypropoxy)-3-methyl-1-phenylpyrazole, U.S. Pat. No. 3,920,691, patented Nov. 18, 1975.

1-(tert.-Butylamino)-3-[(1-phenyl-5-tetrazolyl)oxy]-2-propanol, Antonio, et al., J. Med. Chem. 21, 123-126 (1978).

The latter compound has been previously described in our prior application Ser. No. 789,481.

SUMMARY OF THE INVENTION

The compounds of the present invention are represented by the following formula

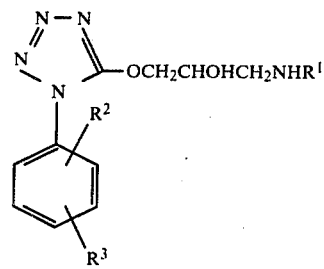

Formula I

In the foregoing formula, $R^1$ is selected from the group consisting of 2-(3-indolyl)-1,1-dimethylethyl, adamantyl, alkyl having 1 to 12 carbon atoms, hydroxyalkyl having 2 to 12 carbon atoms with the hydroxyl group attached to a carbon atom other than that carbon atom attached to the nitrogen atom, alkenyl having 3 to 12 carbon atoms, cycloalkyl having 3 to 6 ring atoms, cycloalkylalkyl having 4 to 12 carbon atoms including 3 to 6 ring atoms, cycloalkenyl having 5 to 6 ring atoms, carbocyclic aralkyl having 7 to 12 carbon atoms, substituted carbocylic aralkyl having 7 to 18 carbon atoms, carbocyclic aryloxyalkyl having 8 to 12 carbon atoms, and substituted carboxyclic aryloxyalkyl having 8 to 18 carbon atoms wherein said substituted aralkyl and said substituted aryloxyalkyl groups each have 1 to 2 ring substitutents selected from the group consisting of halogen, alkoxy having 1 to 6 carbon atoms, alkyl having 1 to 6 carbon atoms, and alkenyl having 3 to 6 carbon atoms, $R^2$ is hydrogen or methyl, and $R^3$ is hydrogen, methyl, halogen including chlorine, bromine, iodine, and fluorine, nitro, or acetamido.

The invention includes compounds having the foregoing structural formula and the acid addition salts thereof. For medical use, the pharmaceutically acceptable acid addition salts are preferred. The pharmaceutically acceptable acid addition salts are those salts in which the anion does not contribute significantly to the toxicity or pharmacological activity of the salt, and as such, they are the pharmacological equivalents of the bases having the foregoing structural formula. In some instances, the salts have physical properties which make them more desirable for pharmaceutical formulation purposes such as solubility, lack of hygroscopicity, compressibility with respect to tablet formation and compatibility with other ingredients with which the substances may be used for pharmaceutical purposes. Acid addition salts which do not meet the foregoing criteria for pharmaceutical acceptability, for instance as to toxicity, are sometimes useful as intermediate for isolation and purification of the present substances or for other chemical synthetic purposes such as separation of optical isomers. Such salts are also part of the invention.

The acid addition salts are made by reaction of a base of the foregoing structural formula with the acid preferably by contact in solution. They may also be made by metathesis or treatment with an anion exchange resin under conditions in which the anion of one salt of the substance is replaced by another anion under conditions which allows for separation of the undesired species such as by precipitation from solution or extraction into a solvent or elution from or retention on an anion exchange resin. Pharmaceutically acceptable acids for the purposes of salt formation include hydrochloric, hydrobromic, hydroiodic, citric, acetic, benzoic, phosphoric, nitric, mucic, isethionic, methanesulfonic, p-toluenesulfonic, glucosaccharic, palmitic, heptanoic, and others.

The compounds of the present invention shown by the foregoing structural formula contain an asymmetric carbon atom in the propanolamine side chain and occur as optically active isomers as well as racemic mixtures thereof. The present invention is intended to include both the optically active and racemic forms. Some of the substances of the present invention contain an asymmetric carbon atom in the $R^1$ substituent, and diastereoisomeric pairs of racemates exist.

Resolution of racemic mixtures to provide the optically active isomers of the foregoing compounds is carried out, for example, by forming a salt with an optically active acid many of which are known to those skilled in the art such as optically active tartaric, mandelic, cholic, 0,0-di-p-toluoyl tartaric, and 0,0-dibenzoyl tartaric acids, or other acids conventionally employed for this purose. The claims, therefore, will be understood to embrace the products in the form of the several racemic mixtures as well as in the form of the optically active isomers where appropriate.

The compounds of the present invention show antiarrhythmic activity, $\beta$-adrenergic blocking activity, and vasodilator activity. They are relatively non-toxic and exert the foregoing physiologic effects at doses substantially below those at which adverse pharmacologic signs are exhibited. Moreover, a substantial margin exists between the doses at which adverse pharmacologic signs are exhibited and those doses which are lethal. Oral or parenteral doses in the range of 2 to 20 mg./kg. are generally suitable.

DETAILED DESCRIPTION OF THE INVENTION

A representative compound of the present invention is the substance of Formula I in which $R^1$ is tert.-butyl, and $R^2$ and $R^3$ are hydrogen. The preparation of this substance is described in Example 1 hereof. This substance is about 1/10 as potent a $\beta$-adrenergic blocking agent as propranolol on a dosage weight basis (conscious rat treated orally; blocking of the hypotension and tachycardia caused by isoproterenol). However, it has outstanding antiarrhythmic activity in animal tests. Antiarrhythmic effects equivalent to those of quinidine sulfate and lidocaine, two substances which are in widespread clinical use as anti-arrhythmic agents, are obtained with substantially lower doses of the substance of Example 1.

Employing the method of Byrne et al., J. Pharmacol. Exp. Therap., Jan. 1977, for evaluating the ability of the compound to abolish ouabain-induced ventricular tachycardia in the dog, the results shown in Table I compared to those for quinidine and lidocaine were obtained.

Table I.

| | Ouabain-Induced Ventricular Tachycardia | | |
|---|---|---|---|
| | Quinidine | Lidocaine | Example 1 |
| MED* | 6 mg/kg (i.v.) | 3 mg/kg (i.v.) | 1 mg/kg (i.v.) |
| End point | normal rhythm | normal rhythm | normal rhythm |
| Duration | >2 hr. | 4–6 min. | >30 min. |
| EKG effects | prolonged QRS | none | none |
| BP effects | decrease 15–20% | decrease 8–12% | none |

*median effective dose

In a surgically-induced arrhythmia in the dog according to the method of Harris, Circulation, 1, 1318 (1950), the substance of Example 1 yielded the results shown in Table II compared to quinidine and lidocaine.

Table II.

| | Occluded Coronary Artery, Dog | | |
|---|---|---|---|
| | Quinidine | Lidocaine | Example 1 |
| MED* | 10 mg/kg (i.v.) | 2 mg/kg (i.v.) | 5 mg/kg (i.v.) |
| Onset | 1 hr. | 1 min. | 5 min. |
| Duration | 6 hr. | 10–12 min. | 4–5 hr. |
| Side effects | ataxia vomiting | agitation | none |

*minimum effective dose to reduce ectopic beats by 50%

The vasodilator action of the present compounds can be demonstrated in the dog hind limb preparation in which the change in perfusion pressure at constant flow rate is measured.

The therapeutic processes of this invention comprise systemic administration of an effective, non-toxic amount of a compound of Formula I or a pharmaceutically acceptable acid addition salt thereof to a mammal having a disease state resulting from excessive stimulation of the $\beta$-adrenergic receptors, or to a mammal requiring vasodilation, or to a mammal having a cardiac arrhythmia or predisposed thereto. An effective amount is constructed to mean a dose which exerts a $\beta$-adrenergic blocking action, a vasodilator effect, or an antiarrhythmic effect without undue toxic side effects. By systemic administration, it is intended to include both oral and parenteral routes. Examples of parenteral administration are intravenous injection or infusion, and intraperitoneal, intramuscular or subcutaneous injection. Rectal administration by ointment or suppository may be employed. Dosage will vary according to the route of administration with from about 0.05 to 100 mg./kg. body weight of 1-(tert.-butylamino)-3-[(1-phenyl-5-tetrazolyl)oxy]-2-propanol or a pharmaceutically acceptable acid addition salt thereof generally providing the desired therapeutic effect. When administered orally, a dose of 0.5 mg./kg. to 10 mg./kg. body weight is preferred.

For the preparation of pharmaceutical compositions containing the compounds of Formula I in the form of dosage units for oral administration, the compound is mixed with a solid, pulverulent carrier such as lactose, sucrose, sorbitol, mannitol, potato starch, corn starch, amylopectin, cellulose derivatives, or gelatin, as well as with glidents such as magnesium stearate, calcium stearate, polyethylene glycol waxes or the like and pressed into tablets. The tablets may be used uncoated or coated by known techniques to delay disintegration and absorption in the gastrointestinal tract and thereby provide a sustained action over a longer period. When coated tablets are wanted, the above prepared core may be coated with a concentrated solution of sugar, which solution may contain e.g. gum arabic, gelatin, talc, titanium dioxide or the like. Furthermore, the tablets may be coated with a lacquer dissolved in an easily volatile organic solvent or mixture of solvents and if desired, dye may be added to this coating.

In the preparation of soft gelatin capsules consisting of gelatin and e.g. glycerine and the like, the active ingredient is mixed with a vegetable oil. Hard gelatin capsules may contain granules of the active ingredient in combination with a solid, pulverulent carrier such as lactose, sucrose, sorbitol, mannitol, starch (such as e.g. potato starch, corn starch, or amylopectin), cellulose derivatives or gelatin.

Dose units for rectal administration may be prepared in the form of suppositories containing the compound in a mixture with a neutral fat base or in the form of a gelatin-rectal capsule with a mixture of vegetable oil or parafin oil.

Liquid preparations suitable for oral administration are suspension, syrups and elixirs containing from about 0.2% by weight to about 20% by weight of the active ingredient.

A suitable injectible composition comprises an aqueous solution of a water soluble pharmaceutically acceptable acid addition salt adjusted to physiologically acceptable pH.

There is also provided by the present invention a process for the preparation of the compounds of Formula I which is outlined in the following reaction scheme in which $R^1$, $R^2$, and $R^3$ have the same meaning as above, and X is chlorine or bromine.

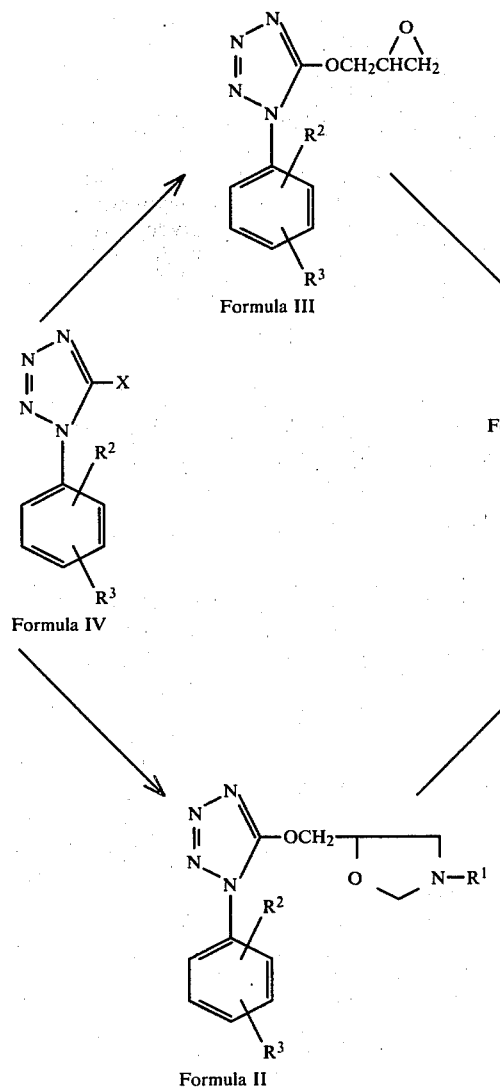

This process employs methods known in the prior art for the preparation of 1-secondary-amino-3-(heterocyclo)oxy-2-propanols as represented by the patents and publications cited in "Description of the Prior Art". The process involves reaction of a 1-($R^2$,$R^3$-phenyl)-5-chloro(or bromo)-1H-tetrazole of Formula IV with either a 3-$R^1$-5-oxazolidinylmethanol or with glycidol both in the presence of a strong base which results in displacement of the halogen atom and formation of an intermediate ether respectively of Formula II or Formula III.

The intermediate of Formula II is converted to the product of Formula I by hydrolysis under acidic conditions. The product of the process is optionally then converted to the base form or acid addition salt form as desired. The hydrolysis of compounds of Formula II is accomplished with dilute mineral acid of from 0.1 N to 1 N concentration at temperatures of from about 20°–100° C. The product can be recovered as the free base by neutralization of the hydrolysis mixture and collecting the precipitate. Acid addition salts may be obtained by evaporating the hydrolysis mixture or by reaction of the free base with acid. Purification is accomplished by conventional means such as recrystallization.

The conversion of the ether of Formula III into the product of Formula I is carried out simply by heating the ether either neat or in the presence of a reaction inert organic solvent with an amine of the formula $R^1NH_2$. No catalyst or condensation agent is required. Suitable solvents include 95% ethanol but other reaction inert organic liquids in which the reactants are soluble may be employed. These include but are not limited to benzene, tetrahydrofuran, dibutyl ether, butanol, hexanol, methanol, dimethoxyethane, ethylene glycol, etc. Suitable reaction temperatures are from about 60°–200° C.

In summary, the present invention provides a process for the preparation of the compounds of Formula I according to which a 1-($R^2$,$R^3$-phenyl)-5-halotetrazole of Formula IV is contacted under reaction conditions with a 3-$R^1$-5-oxazolidinylmethanol or with glycidol to yield, respectively, a 1-($R^2$,$R^3$-phenyl)-5-tetrazolyl ether of Formula II or Formula III and converting said ether into the product of Formula I by hydrolysis under acidic conditions when an ether of Formula II is employed or by reaction at a temperature of 60°s–200° C. with a primary amine of the formula $R^1NH_2$ alone or in the presence of a reaction inert organic solvent when an ether of Formula III is employed. Thereafter, when the substance of Formula I is obtained as the free base, it may be neutralized with a suitable acid to form the acid addition salt. When the substance of Formula I is obtained as the acid addition salt, it may be converted to the free base by neutralization with a base and elimination of the undesired salt of said base produced by the neutralization.

DESCRIPTION OF SPECIFIC EMBODIMENTS

In the following procedures temperatures are expressed in degrees Centigrade. When designated "corr.", melting points are corrected values according to the USP method. The nuclear magnetic resonance (NMR) spectral characteristics refer to chemical shifts (δ) expressed as parts per million (ppm) versus tetramethylsilane as reference standard. The relative area reported for the various shifts corresponds to the number of hydrogen atoms in the individual substituent and the nature of the shift as to multiplicity is reported as broad singlet (bs), singlet (s), multiplet (m), doublet (d), triplet (t), or quadruplet (q) with coupling constant reported where appropriate. The format is NMR (solvent): δ(relative area, multiplicity, J value). Abbreviations employed are EtOH (ethanol), HOAc (acetic acid), Et$_2$O (ethyl ether), DMF (dimethylformamide), MeOH (methanol), i-PrOH (isopropanol), Nujol (mineral oil), DMSOd$_6$ (deuterodimethylsulfoxide), IR (infrared), KBr (potassium bromide), EtOAc (ethyl acetate), d (decomposition), IPE (isopropyl ether). Others are common and have well established meanings. The infrared spectra described include only absorption wave numbers (cm$^{-1}$) having functional group identification value. Unless indicated otherwise, KBr was employed as diluent for IR spectral determinations.

Synthesis of various compounds of Formula I via 3-R$^1$-5-oxazolidinylmethyl ethers of Formula II is illustrated in Examples 1-34.

EXAMPLE 1.
1-tert.-Butylamino-3-[(1-phenyl-5-tetrazolyl)-oxy]-2-propanol.

A solution of 8.0 g. (0.07 mol) of potassium tert.-butoxide and 9.5 g. (0.06 mol) of 3-(tert.-butyl)-5-oxazolidinylmethanol in 250 ml. of THF is heated at reflux for 30 min. 1-Phenyl-5-chlorotetrazole, 10.9 g. (0.06 mol), dissolved in 100 ml. of THF, is then added portionwise during 30 min., and the mixture refluxed for 3 hr. The solvent is then removed by distillation in vacuo to yield a viscous syrup-like residue. This residue contains the intermediate 1-phenyl-5-[3-(tert.-butyl)-5-oxazolidinylmethoxy]-1H-tetrazole which is hydrolyzed by heating for 40 min on the steam bath with 225 ml of 0.3 N HCl. The hydrolysis mixture is filtered, neutralized with NH$_4$OH and chilled to yield the crude base as a white precipitate which is collected. The crude base is converted to the hydrochloride salt by dissolving in Et$_2$O and treatment of the solution with EtOH-HCl, recrystallized from EtOH-EtOAc, mp 152.5°-154.5° (corr.). NMR (CDCl$_3$): 1.46 (9, s); 3.13 (2, m); 4.68 (3, m); 5.64 (1, bs); 7.52 (5, m); 8.30 (1, bs); 9.50 (1, bs). IR: 690, 765, 1460, 1510, 1570, 1600, 2780.

Anal. Found: C, 51.24; H, 6.65; N, 21.43.

EXAMPLES 2-34. Additional 1-(R$^1$NH)-3-[(1-phenyl-5-tetrazolyl)oxy]-2-propanols.

By substitution of various 3-R$^1$-5-oxazolidinylmethanols for 3-(tert.-butyl)-5-oxazolidinylmethanol in the process of Example 1, the following products of the present invention can be prepared.

Table III.

| Example No. | Secondary Amines of Formula I R$^1$ |
|---|---|
| 2 | n-octyl |
| 3 | n-dodecyl |
| 4 | cyclohexyl |
| 5 | 1-methylethyl |
| 6 | n-butyl |
| 7 | allyl |
| 8 | 2-butenyl |
| 9 | cyclopropyl |
| 10 | cyclopentyl |
| 11 | 1-cyclohexenyl |
| 12 | benzyl |
| 13 | 2-phenylethyl |
| 14 | 1-naphthylmethyl |
| 15 | 2-(2-(2-propenyl)-6-methylphenyl)ethyl |
| 16 | 2-(4-methoxyphenyl)ethyl |
| 17 | 2-(3,4-dichlorophenyl)ethyl |
| 18 | 2-(4-hexyloxyphenyl)-1-methylethyl |
| 19 | (4-fluorophenyl)methyl |
| 20 | (4-bromophenyl)methyl |
| 21 | (4-iodophenyl)methyl |
| 22 | 2-(4-tolyl)-2-propyl |
| 23 | 4-(tert.-butyl)-2-naphthyl methyl |
| 24 | 2-(phenoxy)ethyl |
| 25 | 2-(phenoxy)-1-methylethyl |
| 26 | 2-(phenoxy)-1-ethylethyl |
| 27 | 2-(1-naphthoxy-1-ethylethyl |
| 28 | 2-(4-bromophenoxy)ethyl |
| 29 | 2-(4-fluorophenoxy)ethyl |
| 30 | 2-(4-tert.-butylphenoxy)-1-propylethyl |
| 31 | 2-(3-hexyloxyphenoxy)-1-methylethyl |
| 32 | 2-(3-chloro-4-methoxyphenoxy)ethyl |
| 33 | 2-(2-(2-propenyl)-6-methylphenoxy)ethyl |
| 34 | 1-methyl-2-phenethyl |

The 3-R$^1$-5-oxazolidinylmethanols required as starting materials in the foregoing examples may be prepared by known methods, for instance by reductive alkylation of the amine R$^1$NH$_2$ with glyceraldhyde employing a 5% palladium-on-carbon catalyst and methanol or other suitable solvent. When using optically active glyceraldehyde, the optically active end product of Formula I is obtained. When 1-methyl-2-phenethylamine is employed as starting material, 1,2-dihydroxy-3-(1-methyl-2-phenethylamino)propane is obtained. The resulting aminopropane diol is then converted to the desired 3-R$^1$-5-oxazolidinylmethanol by reaction with 37% aqueous formaldehyde in refluxing benzene with continuous removal of the water produced as by-product. In this fashion, 1,2-dihydroxy-3-(1-methyl-2-phenethylamino)propane yields 3-(1-methyl-2-phenethyl)-5-oxazolidinylmethanol.

The synthesis of various 1-(R$^2$,R$^3$-phenyl)-5-chloro (or bromo) tetrazoles of Formula IV, their reaction with glycidol to form glycidyl ethers of Formula III, and reaction of the latter with various R$^1$NH$_2$ primary amines to yield various products of Formula I is illustrated in Examples 35-67.

R$^2$,R$^3$-Substituted Tetrazoles of Formula IV

EXAMPLE 35.
5-Chloro-1-(2,4-dimethylphenyl)tetrazole.

A solution of 2,4-dimethylphenylisonitrile (Ugi, et al., Angew. Chem. Internat. Ed. (Engl.) 4, 472 (1965)) (14.8 g., 0.11 mole) in 100 ml. of acetonitrile was stirred at ice bath temperature while chlorine gas was bubbled in. When tlc indicated that the isonitrile had been consumed, the solvent was removed in vacuo, leaving 22.7 g. of the oily isocyanodichloride. To a solution of the latter in 130 ml. of acetone was added a solution of 7.3 g. (0.11 mole) of sodium azide in 25 ml. of water. After one hour, the acetone was evaporated in vacuo and the aqueous residue was extracted with ethyl acetate. The extract was washed with water and brine, dried (Na$_2$SO$_4$) and evaporated to provide 24.5 g. of a waxy solid. Trituration with isopropyl ether-hexane gave 18.9 g. of the chlorotetrazole, m.p. 75°-77°.

Similar treatment of other isocyanodichlorides yielded the tetrazoles listed in Table IV. Substitution of an isocyanodibromide or of bromine for chlorine in Example 35 yields the corresponding bromo tetrazole intermediate of Formula IV.

Table IV.

| 5-Chloro-1-(R$^2$, R$^3$-phenyl)tetrazole of Formula IV | | | |
|---|---|---|---|
| Example No. | R$^2$, R$^3$ | Recryst. Solvent | m.p. |
| 36 | 2,4-DiMe | IPE-hexane | 75°-77° |
| 37 | 2-Cl, 4-Me | not recrystallized | 101°-102° |
| 38 | 4-Cl | Maggiuli & Paine, U.S. | |

Table IV.-continued

| | 5-Chloro-1-($R^2$, $R^3$-phenyl)tetrazole of Formula IV | | |
|---|---|---|---|
| Example No. | $R^2$, $R^3$ | Recryst. Solvent | m.p. |
| 39 | 4-$NO_2$ | 3,437,665 (1969) Kauer & Sheppard, J. Org. Chem. 32, 3580 (1967) | |
| 40 | 4-NHCOCH$_3$* | not recrystallized | 146°–151° |

*Prepared by acylation of 1-(4-aminophenyl)-5-chloro-1H-tetrazole (Kauer & Sheppard, op. cit.) with acetic anhydride/pyridine (1:1 molar basis) in acetonitrile as solvent.

Table V.

| | Glycidyl Ethers of Formula III | | |
|---|---|---|---|
| Example No. | $R^2$, $R^3$ | Recryst. Solvent | m.p. |
| 42 | H | MeOH-i-PrOH | 83°–84° |
| 43 | 4-Cl | Benzene-Hexane | 88.5°–89° |
| 44 | 4-Cl, 2-Me | Benzene-Hexane | 101°–102° |
| 45 | 2,4-DiMe | i-PrOH | 82.5°–84.5° |
| 46 | 4-$NO_2$ | i-PrOH | 107°–110.5° |
| 47 | 4-NHCOCH$_3$ | EtOH | 169°–170° |

GLYCIDYL ETHERS OF FORMULA III

EXAMPLE 41.

2,3-Epoxy-1-[(1-phenyl-5tetrazolyl)oxy]propane.

Sodium hydride (11.9 g., 0.050 mole), washed free of mineral oil with hexane, was stirred in 1.8 l. of DMF at ice-water temperature while a solution of 72.3 g (0.40 mole) of 1-phenyl-5-chlorotetrazole and 29.6 g. (0.40 mole) of glycidol in 1.8 l. of DMF was added dropwise during 4 hours. The solution was allowed to stand at 25° overnight (16 hours), diluted with 12 l. of H$_2$O and extracted with ethyl acetate. The extracts were washed with water, dried (Na$_2$SO$_4$), and evaporated to give 75.7 g. of product, m.p. 77°–81°. Recrystallization from MeOH-i-PrOH gave 55.8 g., m.p. 83°–84°.

Various 1-($R^2$,$R^3$-phenyl)-5-chloro (or bromo) tetrazoles were converted according to the method of Example 41 to the ethers listed in Table V.

ADDITIONAL PRODUCTS OF FORMULA I

EXAMPLE 48.

1-(tert.-Butylamino)-3-[(1-phenyl-5-tetrazolyl)-oxy]-2-propanol Hydrochloride.

2,3-Epoxy-1-[(1-phenyl-5-tetrazolyl)-oxy]propane (43.7 g., 0.20 mole) was heated at the reflux temperature in 150 ml. of tert.-butylamine and 300 ml. of benzene for 9 hours. The solvents were evaporated in vacuo and the residual oil was dissolved in 100 ml. of EtOH and acidified with ethanolic HCl. Dilution with diethyl ether gave 44.8 g. of the hydrochloride of the product, m.p. 73°–82°. Recrystallization from i-PrOH-IPE gave 30.8 g., m.p. 152.5°–154.5° (corr.).

Similarly prepared were additional examples shown in Table VI. In each instance, elemental analyses for carbon, hydrogen, and nitrogen confirmed the formulas given in the table.

Table VI.

| | Additional Products of Formula I | | | | | | |
|---|---|---|---|---|---|---|---|
| Ex No. | $R^2$,$R^3$ | $R^1$ | Recryst. Solvent | Molecular Formula | m.p.°+ | NMR | IR |
| 49 | H | 1,1-dimethyl-propyl | MeOH-IPE | $C_{14}H_{23}N_5O_2 \cdot$ HCl | 174–176 | (DMSO-d$_6$) 0.89 (3, t, 6.7 Hz) 1.28 (6, s) 1.69 (2, q, 6.7 Hz) 3.08 (2, m) 4.56 (3, m) 6.08 (1, bs) 7.70 (5, m) 8.75 (1, bs) | 688, 760, 1455, 1505, 1570, 1595, 2800, 2970, 3320 |
| 50 | H | 1-adamantyl | MeOH-IPE | $C_{20}H_{27}N_5O_2 \cdot$ HCl | 197.5–198.5 | (DMSO-d$_6$) 1.67 (6, m) 2.00 (9, m) 3.30 (2, m) 4.66 (3, m) 6.22 (1, d, 5.6 Hz) 7.80 (5, m) 9.00 (2, bs) | 690, 760, 1460, 1510, 1575, 1600, 2860, 2930 |
| 51 | H | 1-methylethyl | MeOH-IPE | $C_{13}H_{19}N_5O_2 \cdot$ HCl | 154.5–156.5 | (DMSO-d$_6$) 1.30 (6, d, 6.3 Hz) 3.16 (3, m) 4.66 (3, m) 6.00 (1, bs) 7.80 (5, m) 9.30 (2, bs) | 690, 765, 1445, 1460, 1505, 1575, 1600, 2820, 2980 |
| 52 | H | methyl | MeOH-IPE | $C_{11}H_{15}N_5O_2 \cdot$ HCl | 161–163 | (DMSO-d$_6$) 2.57 (3, s) 3.00 (2, m) 4.40 (3, m) 6.10 (1, bs) 7.69 (5, m) 9.19 (2, bs) | 690, 768, 1000, 1450, 1505, 1570, 1595, 2800, 2960 |
| 53 | H | cyclohexyl-methyl | CH$_3$CN | $C_{17}H_{27}N_5O_2 \cdot$ HCl | 141.5–143.5 | (DMSO-d$_6$) 1.10 (6, m) 1.70 (5, m) 2.92 (4, m) 4.58 (3, m) 6.10 (1, bs) 7.70 (5, m) | 685, 755, 1130, 1450, 1505, 1570, 1595, 2860, 2930, 3290 |

Table VI.-continued
Additional Products of Formula I

| Ex No. | $R^2, R^3$ | $R^1$ | Recryst. Solvent | Molecular Formula | m.p.°+ | NMR | IR |
|---|---|---|---|---|---|---|---|
| 54 | H | cyclohexyl | MeOH-IPE | $C_{16}H_{23}N_5O_2 \cdot HCl$ | 170–171 | (DMSO-$d_6$) 0.9–2.2 (10, m) 3.07 (3, m) 4.51 (3, m) 5.50 (1, bs) 7.70 (5, m) 9.08 (2, bs) 9.10 (2, bs) | 690, 760, 1450, 1460, 1500, 1510, 1570, 1600, 2860, 2960 |
| 55 | H | 1,1,3,3-tetra-methylbutyl | $CH_3CN$-IPE | $C_{18}H_{29}N_5O_2 \cdot HCl$ | 165.5–166.5 | (DMSO-$d_6$) 1.03 (9, s) 1.45 (6, s) 1.71 (2, s) 3.10 (2, m) 4.57 (3, m) 7.71 (5, m) 8.60 (1, bs) 9.15 (1, bs) | 690, 760, 1450, 1505, 1570, 1600, 2800, 2966 |
| 56 | H | cyclopentyl | EtOH | $C_{15}H_{21}N_5O_2 \cdot HCl$ | 160–161.5 | (DMSO-$d_6$) 1.72 (8, m) 3.12 (2, m) 3.51 (1, m) 4.60 (3, m) 6.12 (1, bs) 7.72 (5, m) 9.25 (1, bs) | 690, 760, 1450, 1500, 1570, 1600, 2780, 2960 |
| 57 | H | 2,5-Me$_2$C$_6$H$_3$—OCH$_2$CH(CH$_3$)— | EtOH | $C_{21}H_{27}N_5O_3 \cdot \frac{1}{2}C_2H_2O_4$* | 162–163.5 | (DMSO-$d_6$) 1.28 (3, d, 6.5 Hz) 2.23 (6, s) 3.02 (2, m) 3.36 (1, m) 3.79 (2, m) 4.22 (1, m) 4.64 (2, d, 5.8 Hz) 7.00 (3, m) 7.08 (3, bs) 7.69 (5, m) 9.45 (1, bs) | 685, 760, 1450, 1500, 1565, 1590, 1610, 2960 |
| 58 | H | —C(CH$_3$)$_2$CH$_2$OH | MeOH-IPE | $C_{14}H_{21}N_5O_3 \cdot HCl$ | 132–134 | (DMSO-$d_6$) 1.27 (6, s) 3.16 (2, m) 3.51 (2, s) 4.57 (3, m) 5.72 (2, bs) 7.71 (5, m) 8.52 (1, bs) 9.00 (1, bs) | 685, 755, 1070, 1450, 1500, 1570, 1595, 2780, 2970 |
| 59 | 4-Cl | 1,1-dimethyl-ethyl | EtOH | $C_{14}H_{20}ClN_5O_2 \cdot HCl$ | 181–182 | (DMSO-$d_6$) 1.37 (9, s) 3.16 (2, m) 4.64 (3, m) 6.20 (1, bs) 7.90 (4, m) 9.30 (2, bs) | 830, 1090, 1380, 1500, 1570, 1600, 2800, 2990 |
| 60 | 4-Cl | 1-methylethyl | MeOH-IPE | $C_{13}H_{18}ClN_5O_2 \cdot HCl$ | 181–182 | (DMSO-$d_6$) 1.32 (6, d, 6.4 Hz) 3.18 (3, m) 4.60 (3, m) 5.72 (1, bs) 7.82 (4, m) 9.20 (2, bs) | 840, 1100, 1410, 1450, 1505, 1575, 1600, 2860, 2980, 3340 |
| 61 | 4-Cl | 1,1-dimethyl-propyl | MeOH-IPE | $C_{15}H_{22}ClN_5O_2 \cdot HCl$ | 185.5–186.5 | (DMSO-$d_6$ + CF$_3$COOH (8:1)) 0.86 (3, t, 6.8 Hz) 1.25 (6, s) 1.67 (2, q, 6.8 Hz) 3.11 (2, m) 4.65 (3, m) 7.82 (4, m) 8.85 (2, bs) | 830, 1090, 1455, 1505, 1570, 1600, 2800, 2980 |
| 62 | 4-Cl, 2-Me | 1,1-dimethyl-ethyl | MeOH-IPE | $C_{15}H_{22}ClN_5O_2 \cdot HCl$ | 170–172 | (DMSO-$d_6$) 1.30 (9, s) 2.18 (3, s) 3.06 (2, m) 4.41 (3, m) 5.25 (1, bs) | 820, 880, 1100, 1379, 1455, 1500, 1570, 2780, 2980 |

Table VI.-continued

Additional Products of Formula I

| Ex No. | $R^2,R^3$ | $R^1$ | Recryst. Solvent | Molecular Formula | m.p.°+ | NMR | IR |
|---|---|---|---|---|---|---|---|
| 63 | 2,4-DiMe | 1,1-dimethylethyl | MeOH-IPE | $C_{16}H_{25}N_5O_2 \cdot HCl$ | 172–173 | 7.62 (3, m)<br>9.00 (2, bs)<br>(DMSO-$d_6$)<br>1.30 (9, s)<br>2.11 (3, s)<br>2.38 (3, s)<br>3.02 (2, m)<br>4.30 (3, m)<br>5.60 (1, bs)<br>7.30 (3, m)<br>9.10 (2, bs) | 825, 1030, 1380,<br>1455, 1510, 1570,<br>2780, 2980 |
| 64 | 4-NO$_2$ | 1,1-dimethylethyl | MeOH-IPE | $C_{14}H_{20}N_6O_4 \cdot HCl$ | 171–172 | (DMSO-$d_6$)<br>1.33 (9, s)<br>3.10 (2, m)<br>4.58 (3, m)<br>8.33 (4, m)<br>8.80 (1, bs)<br>9.30 (1, bs) | 750, 850, 1350,<br>1450, 1500, 1530,<br>1570, 1600, 1615,<br>2980 |
| 65 | H | 3,4-MeO$_2$C$_6$H$_3$CH$_2$— | | $C_{19}H_{23}N_5O_4 \cdot C_4H_4O_4$ | 175–176 | (DMSO-$d_6$)<br>3.10 (2, m)<br>3.82 (6, s)<br>4.20 (2, s)<br>4.64 (3, m)<br>6.25 (2, s)<br>7.50 (5, m) | 685, 758, 1025,<br>1260, 1460, 1520,<br>1570, 1600, 1700,<br>2830 |
| 66 | 4-NHCOCH$_3$ | tert.-Bu | MeOH-IPE | $C_{16}H_{24}N_6O_3 \cdot HCl \cdot \frac{1}{4}H_2O$ | 185–186 | (DMSO-$d_6$)<br>1.33 (9, s)<br>2.11 (3, s)<br>3.10 (2, m)<br>4.51 (3, m)<br>6.04 (1, bs)<br>7.76 (4, m)<br>8.90 (2, bs)<br>10.46 (1, bs) | 835, 1315, 1410,<br>1520, 1540, 1570,<br>1600, 1675, 2980 |
| 67 | H | 2-(3-indolyl)-1,1-dimethylethyl | | | | | |

+ °C. (corr.)
*hemi-oxalate maleate

EXAMPLE 68. Tablets.

The following ingredients are blended in the proportion by weight indicated according to conventional pharmaceutical techniques to provide a tablet base.

| Ingredient | Amount |
|---|---|
| Lactose | 79 |
| Corn starch | 10 |
| Talcum | 6 |
| Tragacanth | 4 |
| Magnesium stearate | 1 |

This tablet base is blended with sufficient 1-(tert.-butylamino)-3-[(1-phenyl-5-tetrazolyl)oxy]-2-propanol or a pharmaceutically acceptable acid addition salt thereof to provide tablets containing 10, 20, 40, 80, 160 and 320 mg. of active ingredient, and compressed in a conventional tablet press. Other compounds of Examples 2-34, or 48-67 may be substituted as active ingredient.

EXAMPLE 69. Dry Filled Capsules.

The following ingredients are blended in a conventional manner in the proportion by weight indicated.

| Ingredient | Amount |
|---|---|
| Lactose, U.S.P. | 50 |
| Starch | 5 |
| Magnesium stearate | 2 |

Sufficient 1-(tert.-butylamino)-[(1-phenyl-5-tetrazolyl)-oxy]-2-propanol or a pharmaceutically acceptable acid addition salt thereof is added to the blend to provide capsules containing 10, 20, 40, 80, 160 and 320 mg. of active ingredient which is filled into hard gelatin capsules of a suitable size. Other compounds of Examples 2-34, or 48-67 may be substituted as active ingredient.

EXAMPLE 70. Solution.

A solution of 1-(tert.-butylamino)-[(1-phenyl-5-tetrazolyl)oxy]-2-propanol hydrochloride is prepared from the following ingredients.

| Ingredient | Amount |
|---|---|
| Active ingredient | 20 g. |
| Sucrose, U.S.P. | 400 g. |
| Sorbitol, U.S.P. | 100 g. |
| Bentonite | 20 g. |
| Flavors, q.s. | |
| Water, q.s. to make 1 liter | |

Each milliliter of the suspension contains approximately 20 mg. of the active ingredient.

Various of the products of Examples 2-34, and 48-67 were evaluated as anti-arrhythmic agents in ouabain-induced ventricular tachycardia according to the method of Byrne, et al., op cit. The observations made are arranged in Table VII.

Table VII.

| | Ouabain-Induced Ventricular Tachycardia | | | | |
|---|---|---|---|---|---|
| Example No. | MED[1] (mg/kg) | Activity Ratio[2] | Duration | EKG Effects | BP Effects |
| 1, 48 | 1 | 6/7 | >30 min. | none | none |
| 49 | 2 | 3/3 | >30 min. | none | ↓33% |
| 65 | 10 | 1/3 | >30 min. | bradycardia | none |
| 50 | 3 | 2/2 | >30 min. | none | none |
| 59 | 2 | 3/3 | 3 min. | none[3] | ↓70% |
| 60 | 4 | 2/2 | >30 min. | none | ↓20% |
| 5, 51 | 5 | 2/2 | >30 min. | none | ↓20% |
| 61 | 2 | 2/2 | >30 min. | none | none |
| 62 | 12 | 2/3 | >30 min. | none | none |
| 63 | 7 | 2/2 | 20 min. | none | ↓10% |
| 52 | 13 | 2/2 | >30 min. | none | ↓10% |
| 53 | 10 | 2/2 | >30 min. | none | none |
| 4, 54 | 2 | 2/2 | >30 min. | none | ↓20% |
| 55 | 5 | 2/2 | >30 min. | none | none |
| 10, 56 | 3 | 2/2 | >30 min. | none | none |
| 57 | 5 | 2/2 | >30 min. | none | none |
| 58 | 5 | 3/3 | >30 min. | bradycardia | none |
| 64 | 3 | 2/2 | >30 min. | none | none |

[1]minimum effective dose to convert to normal rhythm.
[2]number of dogs converted to normal rhythm/number of dogs tested.
[3]one dog died.

Certain of these substances were also evaluated against the surgically-induced arrhythmia in the dog according to the method Harris, op cit. The observations made are arranged in Table VIII.

Table VIII.

| | Occluded Coronary Artery, Dog | | | | |
|---|---|---|---|---|---|
| Example No. | MED$_{50}$[1] | MED$_{100}$[1] | Onset | Duration | Side Effects |
| 1, 48 | 5 | >10 | 1 min. | >6 hr. | none |
| 1, 48 | 20[2] | 40[2] | 30 min. | >6 hr. | none |
| 49 | — | 5 | 1 min. | 30 min. | 2/5 died |
| 65 | — | 10 | 2 min. | 30 min. | trembling & agitation & diarrhea |
| 65 | 20[2] | >20[2] | 2 hr. | 4.5 hr. | none |
| 50 | 10 | >10 | 2 min. | 6 hr. | none |
| 59 | >10 | >10 | — | — | none |
| 60 | >10 | >10 | — | — | vomiting |
| 5, 51 | 20 | >20 | 2 min. | 30 min. | ataxia |
| 61 | 5 | 10 | 5 min. | 1.5 hr. | 1/5 died |

[1]minimum effective dose, 50% and 100% reduction of ectopic beats, intravenous administration mg/kg. body weight.
[2]oral dose, mg/kg. body weight.

What is claimed is:
1. A compound having the formula the pharmaceutically acceptable acid addition salts thereof wherein
$R^1$ is selected from the group consisting of 2-(3-indolyl)-1,1-dimethylethyl, adamantyl, alkyl having 1 to 12 carbon atoms, hydroxyalkyl having 2 to 12 carbon atoms having the hydroxyl group attached to a carbon atom other than that carbon atom attached to the nitrogen atom, alkenyl having 3 to 12 carbon atoms, cycloalkyl having 3 to 6 ring atoms, cycloalkylalkyl having 4 to 12 carbon atoms including 3 to 6 ring atoms, cycloalkenyl having 5 to 6 ring atoms, carbocyclic aralkyl having 7 to 12 carbon atoms, substituted carbocyclic aralkyl having 7 to 18 carbon atoms, carbocyclic aryloxyalkyl having 8 to 12 carbon atoms, and substituted carbocyclic aryloxyalkyl having 8 to 18 carbon atoms wherein said substituted aralkyl and said substituted aryloxyalkyl groups each have 1 or 2 ring substituents selected from the group consisting of halogen, alkoxy having 1 to 6 carbon atoms, alkyl having 1 to 6 carbon atoms, and alkenyl having 3 to 6 carbon atoms wherein said ring substituents are sterically compatible;
$R^2$ is hydrogen or methyl, and
$R^3$ is hydrogen, methyl, halogen, nitro, or acetamido.

2. A compound of claim 1 wherein $R^1$ is alkyl having 1 to 12 carbon atoms, and $R^2$ and $R^3$ are hydrogen, and the pharmaceutically acceptable acid addition salts thereof.

3. A compound of claim 1, 1-(methylamino)-3-[(1-phenyl-1H-tetrazol-5-yl)oxy]-2-propanol and the pharmaceutically acceptable acid addition salts thereof.

4. A compound of claim 1 wherein $R^1$ is branched alkyl having 3 to 8 carbon atoms, and $R^2$ and $R^3$ are hydrogen, and the pharmaceutically acceptable acid addition salts thereof.

5. The compound of claim 1, 1-(tert.-butylamino)-3-[(1-phenyl-5-tetrazolyl)oxy]-2-propanol, and the pharmaceutically acceptable acid addition salts thereof.

6. The compound of claim 1, 1-[(1,1-dimethylpropyl)amino]-3-[(1-phenyl-1H-tetrazol-5-yl)oxy]-2-propanol, and the pharmaceutically acceptable acid addition salts thereof.

7. The compound of claim 1, 1-[(1-methylethyl)amino]-3-[(1-phenyl-1H-tetrazol-5-yl)oxy]-2-propanol, and the pharmaceutically acceptable acid addition salts thereof.

8. The compound of claim 1, 1-[(1-phenyl-1H-tetrazol-5-yl)-oxy]-3-[(1,1,3,3-tetramethylbutyl)amino]-2-propanol, and the pharmaceutically acceptable acid addition salts thereof.

9. A compound of claim 1 wherein $R^1$ is cycloalkyl having 3 to 6 ring atoms, and $R^2$ and $R^3$ are hydrogen, and the pharmaceutically acceptable salts thereof.

10. The compound of claim 1, 1-(cyclohexylamino)-3-[(1-phenyl-1H-tetrazol-5-yl)oxy]-2-propanol, and the pharmaceutically acceptable acid addition salts thereof.

11. The compound of claim 1, 1-(cyclopentylamino)-3-[(1-phenyl-1H-tetrazol-5-yl)oxy]-2-propanol, and the pharmaceutically acceptable acid addition salts thereof.

12. A compound of claim 1 wherein $R^1$ is cycloalkenyl having 5 to 6 ring atoms, and $R^2$ and $R^3$ are hydrogen, and the pharmaceutically acceptable salts thereof.

13. A compound of claim 1 wherein $R^1$ is carbocyclic aralkyl having 7 to 12 carbon atoms, and $R^2$ and $R^3$ are hydrogen, and the pharmaceutically acceptable salts thereof.

14. A compound of claim 1 wherein $R^1$ is carbocyclic aryloxyalkyl having 8 to 12 carbon atoms, and $R^2$ and $R^3$ are hydrogen and the pharmaceutically acceptable salts thereof.

15. A compound of claim 1 wherein $R^2$ and $R^3$ are hydrogen, and $R^1$ is substituted carbocyclic aralkyl having 7 to 18 carbon atoms and 1 or 2 ring substituents selected from halogen, alkoxy having 1 to 6 carbon atoms, alkyl having 1 to 6 carbon atoms, and alkenyl having 3 to 6 carbon atoms, and the pharmaceutically acceptable salts thereof wherein said ring substituents are sterically compatible.

16. The compound of claim 1, 1-[[(3,4-dimethoxyphenyl)methyl]amino]-3-[(1-phenyl-1H-tetrazol-5-yl)oxy]-2-propanol, and the pharmaceutically acceptable acid addition salts thereof.

17. A compound of claim 1 wherein $R^2$ and $R^3$ are hydrogen, and $R^1$ is substituted carbocyclic aryloxyalkyl having 8 to 18 carbon atoms and 1 or 2 ring substituents selected from halogen, alkoxy having 1 to 6 carbon atoms, alkyl having 1 to 6 carbon atoms, and alkenyl having 3 to 6 carbon atoms, and the pharmaceutically acceptable salts thereof wherein said ring substituents are sterically compatible.

18. The compound of claim 1, 1-[2-(2,6-dimethylphenoxy)-1-methylethyl]amino]-3-[(1-phenyl-1H-tetrazol-5-yl)oxy]-2-propanol, and the pharmaceutically acceptable acid addition salts thereof.

19. A compound of claim 1 wherein $R^1$ is alkenyl having 3 to 12 carbon atoms, $R^2$ and $R^3$ are hydrogen, and the pharmaceutically acceptable acid addition salts thereof.

20. A compound of claim 1 wherein $R^1$ is cycloalkylalkyl having 4 to 12 carbon atoms including 3 to 6 ring atoms, and $R^2$ and $R^3$ are hydrogen, and the pharmaceutically acceptable acid addition salts thereof.

21. The compound of claim 1, 1-[(cyclohexylmethyl)amino]-3-[(1-phenyl-1H-tetrazol-5-yl)oxy]-2-propanol, and the pharmaceutically acceptable acid addition salts thereof.

22. The compound of claim 1, 1-(1-adamantylamino)-3[(1-phenyl-1H-tetrazol-5-yl)oxy]-2-propanol, and the pharmaceutically acceptable acid addition salts thereof.

23. A compound of claim 1 wherein $R^1$ is branched chain alkyl having 3 to 8 carbon atoms, $R^2$ is hydrogen, and $R^3$ is chlorine, and the pharmaceutically acceptable acid addition salts thereof.

24. The compound of claim 1, 1-[[1-(4-chlorophenyl)-1H-tetrazol-5-yl]oxy]-3-[(1,1-dimethylethyl)amino]-2-propanol, and the pharmaceutically acceptable acid addition salts thereof.

25. The compound of claim 1, 1-[[1-(4-chlorophenyl)-1H-tetrazol-5-yl]oxy]-3-[(1-methylethyl)amino]-2-propanol, and the pharmaceutically acceptable addition salts thereof.

26. The compound of claim 1, 1-[[1-(4-chlorophenyl)-1H-tetrazol-5-yl]oxy]-3-[(1,1-dimethylpropyl)amino]-2-propanol, and the pharmaceutically acceptable acid addition salts thereof.

27. A compound of claim 1 wherein $R^1$ is branched chain alkyl having 3 to 8 carbon atoms, $R^2$ is hydrogen, and $R^3$ is nitro, and the pharmaceutically acceptable acid addition salts thereof.

28. The compound of claim 1, 1-[(1,1-dimethylethyl)amino]-3-[[1-(4-nitrophenyl)-1H-tetrazol-5-yl]oxy]-2-propanol, and the pharmaceutically acceptable acid addition salts thereof.

29. The compound of claim 1, 1-[[1-(4-chloro-2-methylphenyl)-1H-tetrazol-5-yl]oxy]-3-[(1,1-dimethylethyl)amino]-2-propanol, and the pharmaceutically acceptable acid addition salts thereof.

30. The compound of claim 1, 1-[(1,1-dimethylethyl)amino]-3-[[1-(2,4-dimethylphenyl)-1H-tetrazol-5-yl]oxy]-2-propanol, and the pharmaceutically acceptable acid addition salts thereof.

31. The compound of claim 1, 1-[(2-hydroxy-1,1-dimethylethyl)-amino]-3-[(1-phenyl-1H-tetrazol-5-yl)oxy]-2-propanol, and the pharmaceutically acceptable acid addition salts thereof.

32. The compound of claim 1, 3-[[1-(4-acetamidophenyl)-1H-tetrazol-5-yl]oxy]-1-[(1,1-dimethylethyl)amino]-2-propanol, and the pharmaceutically acceptable acid addition salts thereof.

* * * * *